United States Patent
Sears

[11] Patent Number: 6,140,304
[45] Date of Patent: Oct. 31, 2000

[54] METHOD OF AND NUTRITIONAL AND PHARMACEUTICAL COMPOSITIONS FOR REDUCTION OF HYPERINSULINEMIA

[75] Inventor: Barry D. Sears, Swampscott, Mass.

[73] Assignee: Eicotech Corporation, Boston, Mass.

[21] Appl. No.: 07/996,797

[22] Filed: Dec. 24, 1992

Related U.S. Application Data

[63] Continuation-in-part of application No. 07/771,058, Oct. 2, 1991, abandoned, and application No. 07/771,402, Oct. 2, 1991, abandoned, each is a continuation-in-part of application No.07/539,384, Jun. 18, 1990, Pat. No. 5,059,622, which is a division of application No. 07/400,288, Aug. 29, 1989, abandoned, which is a continuation-in-part of application No. 07/251,139, Sep. 28, 1988, abandoned.

[51] Int. Cl.$^7$ .......................... A61K 38/00; A61K 31/70; A61K 31/22; A61K 31/23; A61K 31/20
[52] U.S. Cl. .................................. 514/2; 514/23; 514/549; 514/552; 514/560
[58] Field of Search ...................................... 514/549, 552, 514/560, 866, 2, 23

[56] References Cited

U.S. PATENT DOCUMENTS

| | | | |
|---|---|---|---|
| 4,826,877 | 5/1989 | Stewart et al. .......................... | 514/549 |
| 4,921,877 | 5/1990 | Cashmere et al. ...................... | 514/866 |

OTHER PUBLICATIONS

The Merck Manual (14$^{th}$ edition) 1982, p. 388.

*Primary Examiner*—Raymond Henley, III
*Attorney, Agent, or Firm*—Dechert Price & Rhoads

[57] ABSTRACT

A method and nutritional and pharmaceutical compositions are provided for the reduction of hyperinsulinemia and the improvement of disease conditions related to hyperinsulinemia by administering a nutritional composition to modify hormonal response.

16 Claims, 5 Drawing Sheets

METHOD OF AND NUTRITIONAL AND PHARMACEUTICAL COMPOSITIONS FOR REDUCTION OF HYPERINSULINEMIA

REFERENCE TO PRIOR APPLICATIONS

This application is a continuation-in-part application of U.S. patent applications Ser. No. 07/771,058 filed Oct. 2, 1991, now abandoned, and Ser. No. 07/771,402, filed Oct. 2, 1991, now abandoned, which applications are both continuation-in-part applications of U.S. Ser. No. 07/539,384, filed Jun. 18, 1990, now U.S. Pat. No. 5,059,622, issued Oct. 22, 1991, which application is a divisional of U.S. Ser. No. 07/400,288, filed Aug. 29, 1989, now abandoned, which application is a continuation-in-part of U.S. Ser. No. 07/251,139, filed Sep. 28, 1988, now abandoned. All are incorporated by reference herein.

FIELD OF THE INVENTION

The present invention relates to both nutritional and pharmaceutical compositions containing specified activated Omega 6 essential fatty acids, such as gamma linolenic acid (GLA) and/or dihomo gamma linolenic acid (DGLA), combined with the activated Omega 3 essential fatty acids, such as eicosapentaenoic acid (EPA), for the modulation of prostaglandin levels in order to reduce hyperinsulinemia. Although certain ratios of activated Omega 6 essential fatty acids and Omega 3 essential fatty acids can achieve this result, the modulation of prostaglandin levels can be enhanced when the appropriate ratio of activated essential fatty acids are combined with the appropriate ratios of protein and carbohydrate to control the postprandial secretion of insulin and glucagon. This invention can provide effective treatment for existing disease conditions which are related to hyperinsulinemia.

BACKGROUND OF THE INVENTION

Prostaglandins are a group of hormone-like substances which are known to play a critical role in virtually all body functions, including the control of the endocrine system, including insulin secretion. Elevated levels of insulin (i.e. hyperinsulinemia) are known to be strongly correlated with cardiovascular conditions such as hypertension, hyperlipidemia, Type II diabetes, and obesity [Reaven, G. M. *Diabetes* 37 1595–1607 (1988)]. The reduction of hyperinsulinemia results in a significant reduction of symptoms associated with any of these associated cardiovascular conditions.

Prostaglandins are directly effected by the diet. The role of diet in prostaglandin production is critical since the precursors of prostaglandins, known as essential fatty acids, cannot be made by humans and therefore must be supplied in the diet. Essential fatty acids are classified as either Omega 6 or Omega 3 depending on the positioning of their unsaturated double bonds within the fatty acid molecule. The typical essential fatty acids found in the diet are linoleic acid, (an Omega 6 essential fatty acid), and alpha linolenic acid (an Omega 3 essential fatty acid). However, the essential fatty acids normally found in the diet are not the actual precursors to prostaglandins. The body must further metabolize these commonly available essential fatty acids into more metabolically activated essential fatty acids. The rate limiting step in this further metabolism is controlled by the enzyme delta 6 desaturase. Once an essential fatty acid has progressed beyond this enzymatic rate determining step, it has a far greater impact on prostaglandin metabolism. We term essential fatty acids beyond this enzymatic step as "activated essential fatty acids".

U.S. Pat. No. 5,059,622 discloses that the ratio of activated Omega 6 essential fatty acids [such as gamma linolenic acid (GLA) or dihomo gamma linolenic acid (DGLA)] and activated Omega 3 essential fatty acids, such as eicosapentaenoic acid (EPA), will have a significant impact on the production of prostaglandins of the one series or production of prostaglandins of the two series. Prostaglandins of the one series (derived from DGLA) such as $PGE_1$, have a beneficial impact on the cardiovascular system, whereas prostaglandins of the two series (derived from arachidonic acid [AA]) such as thromboxane $A_2$ often have an adverse impact on the cardiovascular system. It is the dynamic balance of these two classes of prostaglandins, which is controlled by the diet, which will be a major factor in determining cardiovascular function.

The importance of maintaining an appropriate balance of prostaglandins of the one and two series is ultimately controlled by maintaining an optimal ratio of DGLA to AA. The ratio of DGLA to AA can be controlled through the dietary intake of the ratio of activated Omega 3 and Omega 6 essential fatty acids was disclosed in U.S. Pat. No. 5,059,622. It has been disclosed in U.S. Pat. No. 5,059,622 that the balance of activated Omega 3 essential fatty acids (in particular eicosapentaenoic acid or EPA) and activated Omega 6 essential fatty acids (either GLA or DGLA) has an impact on prostaglandin formation and the resulting reduction of hypertension. The appropriate ratio of EPA combined with gamma linolenic acid (GLA) or dihomo gamma linoleic acid (DGLA) would increase the amount of prostaglandins of the one series (such as $PGE_1$) which are vasodilators while decreasing the relative amounts of prostaglandins of the two series (such as thromboxane $A_2$) which are vasoconstrictors. The end result of this prostaglandin modulation would be reflected in the reduction of hypertension.

SUMMARY OF THE INVENTION

This invention comprises a method of and nutritional and pharmaceutical compositions for the treatment of hyperinsulinemia by altering the hormonal response caused by dietary factors. In particular, this invention relates to the reduction of hyperinsulinemia, and therefore the control of resulting disease conditions that are strongly associated with hyperinsulinemia.

Although prostaglandins are the primary regulators of the cardiovascular system, the also play a significant role in the regulation of other hormonal systems. An example of these effects on the endocrine system is that prostaglandins have a significant effect on the release of insulin from the pancreas. Thus reduction of hyperinsulinemia can be achieved by the appropriate modulation of prostaglandins, and in particular by increasing the prostaglandins of the one series while simultaneously decreasing those of the two series. This is because prostaglandins of the one series, and in particular $PGE_1$, have an inhibitory effect on the release of insulin [Sacca, L et. al., *Acta Endocrinologica* 79 266–274 (1975)].

This modulation of prostaglandins can be accomplished by the supplementation of the diet with the appropriate ratio of activated Omega 6 essential fatty acids and the activated Omega 3 essential fatty acids. This modulation of prostaglandins can be further enhanced by the simultaneous ingestion of the appropriate combination of protein to carbohydrate in a solid food format to control the postprandial ratio of insulin to glucagon. The control of the postprandial ratio of insulin to glucagon will further enhance the production of prostaglandins of the one series while decreasing the prostaglandins of the two series because of the effects that insulin and glucagon have the the key enzyme to modulates prostaglandin production. This combination of nutritional factors will maximize the production of the preferred series of prostaglandins for reduction of hyperinsulinemia.

DETAILED DESCRIPTION OF THE INVENTION

It has been long recognized that cardiovascular disease and the risk factors (such as hypertension, hyperlipidemia, increased platelet aggregation, Type II diabetes, and obesity) associated with cardiovascular disease are related to elevated levels of insulin, which leads to a corresponding development of insulin resistance (see Reaven ref). The severity of these disease states are significantly mitigated, if not eliminated by the reduction of elevated insulin levels in the patient. This invention relates to the control of elevated insulin levels by modulation of prostaglandins and the nutritional compositions that maximizes this effect. The combination of these nutritional combinations will have a synergistic effects to further enhance the production of prostaglandins of the one series (such as $PGE_1$). This increase in $PGE_1$ levels will in turn normalize (by reducing insulin secretion) the elevation of serum insulin that characterizes hyperinsulinemia. As a result, those disease states (such as hypertension) that are related to hyperinsulinemia will have a significant reduction of the severity of the symptoms that characterize them. Therefore, a reduction of the symptoms in disease states related to hyperinsulinemia would be indicative of the reduction of hyperinsulinemia itself.

The role of diet in the development and the treatment of cardiovascular disease has long been recognized. What has not been recognized is the effect that certain dietary compositions have upon hormonal responses that are directly related to dietary intake. It is often the disturbance of these hormonal balances that have a very dramatic impact on the progression of cardiovascular disease. Therefore, controlling those hormonal responses which are a direct consequence of the diet will have a strong influence on treatment of various cardiovascular disease conditions.

This invention extends U.S. Pat. No. 5,059,622 to modulate the production of prostaglandins of one or two series in order to reduce hyperinsulinemia. In addition, this modulation of prostaglandins achieved by the dietary intake of the appropriate ratio of activated Omega 6 and Omega 3 essential fatty acids can be enhanced with the simultaneous administration of the appropriate ratio of protein, carbohydrate, and fat in a solid food format.

The reason for the critical need to control the ratio of protein to carbohydrate is that their ratio in a meal will cause transitory changes after a meal (i.e. postprandial) in the extent of insulin and glucagon secretion. The control of the postprandial ratio of insulin and glucagon will effect the activity of the key enzyme (delta 5 desaturase) which controls the rate of metabolism of DGLA into AA (Brenner, R. R. Prog. *Lipid Res.* 20 41–47 [1982]). The activity of this enzyme thus profoundly effects which classes of prostaglandins are produced (see FIG. 1). In particular, insulin increases the activity of delta 5 desaturase (thereby increasing the production of AA and decreasing the levels of DGLA), whereas glucagon decreases its activity (thereby increasing DGLA levels and reducing the production of AA). The ratio of DGLA to AA determines the extent of the production of prostaglandins of one series or two series. An illustration of this adverse effect of increased insulin secretion on arachidonic acid production was shown by Pelikanova et al. [Pelikanova, T. et al. *Clinica Chimica Acta* 203 329–338 (1991)] in which sustained insulin levels over a four hour period caused a significant increase in the serum levels of arachidonic acid. This indicates the critical need to control insulin during the usual four hour postprandial elevation of insulin and glucagon levels for the maximizing the modulation of prostaglandin production that results from the dietary intake of activated essential fatty acids.

It has also been shown by Konrad et al. [Konrad, R. J. et al. *Biochim. Biophys. Acta* 1135 215–220 (1992)], that insulin induced arachidonic acid (AA) production will further increase insulin secretion which is contrary to the purpose of this invention. Therefore the control of the ratio of DGLA to AA (which is controlled by the activity of the delta 5 desaturase enzyme) will play a key role in the reduction of hyperinsulinemia, since it is this ratio that determines which series of prostaglandins are produced.

The control of the postprandial balance of insulin to glucagon is a direct consequence of the composition of the macronutrients (i.e. protein, carbohydrate, and fat) in a meal. The postprandial secretion of insulin and glucagon are a direct consequence of the ratio of protein to carbohydrate in a meal [Westphal, S. A, et al. *Am J. Clin. Nutr.* 52 267–272 (1990)]. It was shown by Wesphal et al. that the postprandial rise in insulin and glucagon levels is profoundly effected by the dietary ratio of protein to carbohydrate consumed in a meal.

Insulin is paired in the bloodstream with glucagon. If insulin levels rise, then glucagon levels fall, and vicesa versa. Therefore in hyperinsulinemia the ratio of insulin to glucagon will be higher than normal, thus decreasing the ratio of DGLA to AA. One excellent indicator of hyperinsulinemia is the presence of excess body fat. This is because insulin accelerates the storage of fat in the adipose tissue, whereas glucagon is responsible for the mobilization of stored body fat for metabolic energy. This is why the development of excess body fat is considered an early risk factor for the development of cardiovascular disease since fat accumulation is strongly associated with hyperinsulinemia.

The present invention provides a method and nutritional composition for treatment of individuals with hyperinsulinemia by modulating prostaglandin levels by supplying the appropriate ratio of activated Omega 6 essential fatty acids and activated Omega 3 essential fatty acids. This invention can be enhanced by controlling the postprandial secretion of insulin and glucagon during the oral administration of the activated Omega 6 and Omega 3 essential fatty acids.

To achieve this control of macronutrient flow, I have discovered that the nutritional composition of the protein, carbohydrate, and fat must be in the form of a solid product not only to increase residence time in the stomach, but also decrease its digestion rate prior to absorption. Enteral (i.e. liquid) formulations will have a very limited residence time in the stomach before the contents are emptied into the duodenum for the final digestive process and then absorption primarily in the small intestine. The digestion time of any food product is related to its surface area. An enteral formulation presents a maximum surface area which facilitates digestion, whereas a solid product with a much smaller surface area for the same amount of macronutrients will have a reduced absorption rate due to a slower gastric emptying and digestion rate. It is also known that fat decreases the rate of gastric emptying which in turn reduces the rate of entry of the carbohydrate into the bloodstream and the corresponding insulin response [Welch, I. McL. et al. Clin Sci. 72 209–216 (1987)].

The rate and extent of postprandial insulin secretion is primarily a consequence of the carbohydrate content of a meal (see FIG. 2). Whereas the postprandial secretion of glucagon is primarily controlled by the protein content of a meal. This is why the protein to carbohydrate ratio in the solid format is of critical importance to control the resulting hormonal response for optimal modulation of prostaglandin production that comes from the dietary intake of the activated essential fatty acids. Furthermore, the solid food enhancement of the invention should consist of the appropriate amount of fat to further facilitate the desired postprandial effects on insulin and glucagon levels. This is because fat will retard the gastric emptying of carbohydrates into the bloodstream thereby further reducing insulin secretion, thus increasing the postprandial glucagon to insulin ratio. Therefore, the correct ratios of protein, carbohydrate, and fat in the solid food format enhancement to the invention will provide a more precise modulation of prostaglandin production by the postprandial control of insulin and glucagon levels. The control of this insulin to glucagon ratio will in turn maximize the modulation of prostaglandins produced from the simultaneous intake of the appropriate ratio of activated Omega 6 and Omega 3 essential fatty acids.

The physical state of the macronutrients is critical to the success of the solid food enhancement to the invention by controlling the postprandial ratio of insulin to glucagon balance that results after digestion. This is why an enteral or liquid product with the same macronutrient composition will not have the desired physiological results as the solid food format. This is because an enteral or liquid form with the same composition will not have the ability to control the entry rates of the macronutrients into the bloodstream because of (1) its rapidity of gastric emptying and (2) the ease of digestion due to its greater surface area it presents to the digestive enzymes. Thus an enteral form will not enhance the benefits of the appropriate ratio of activated essential fatty acids, and in fact may be detrimental (by potentially increasing insulin secretion [see FIG. 3]) to the individual with regard to the ability to control activated essential fatty acid supplementation to modulate prostaglandin production.

Dietary control of DGLA and AA using this invention will ultimately determine whether prostaglandins of the one or two series will be formed. The reduction of hyperinsulinemia can be achieved by the modulation of prostaglandins, and in particular by increasing the prostaglandins of the one series while decreasing those of the two series. This modulation can be accomplished by the supplementation of the diet with the appropriate ratio of activated Omega 6 essential fatty acids (such as GLA and DGLA) and activated Omega 3 essential fatty acids that can be converted into EPA (such as stearidonic acid or docosahexenoic acid). This modulation of prostaglandins can be further enhanced by the appropriate combination of protein to carbohydrate in a solid format to control the postprandial ratio of insulin to glucagon. This combination of these nutritional factors will maximize the production of the preferred prostaglandins of the one series for reduction of hyperinsulinemia.

As disclosed in U.S. Pat. No. 5,059,622, if GLA is supplied in the diet appropriate amounts of EPA must also be present to promote the production of beneficial prostaglandins (i.e. those of the one series) by inhibiting the rate of formation of arachidonic acid since EPA is a feedback inhibitor of the enzyme delta 5 desaturase. In this invention, if the postprandial control of the balance of insulin to glucagon is being controlled by the solid food format, then less EPA relative to GLA will be required for the effective inhibition of delta 5 desaturase activity, thereby controlling the appropriate balance of DGLA to AA required for beneficial prostaglandin production. As a consequence, a lesser amount of EPA relative to GLA will be required to modulate the production of beneficial prostaglandins of the one series if the appropriate protein to carbohydrate ratio in a solid format is supplied at the same time as the activated essential fatty acids.

DETAILED DESCRIPTION OF THE FIGURES

Figure 1:
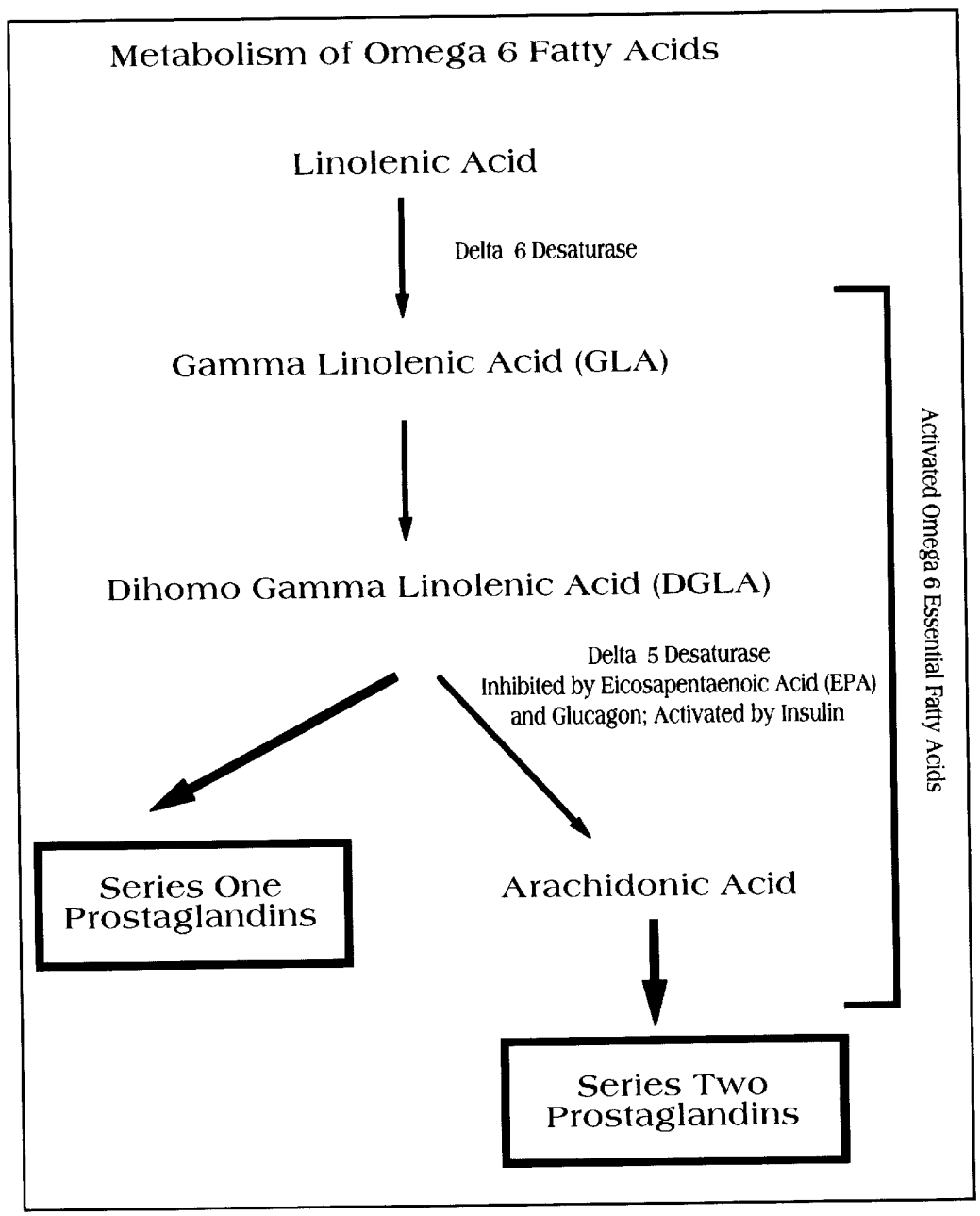
FIG. 1 is a schematic flow diagram of the metabolism of omega 6 essential fatty acids and their further metabolism of prostaglandins of the one series and two series.

The importance of controlling the protein to carbohydrate ratio for the modulation of prostaglandin response is shown in FIG. 1. The key enzyme (delta 5 desaturase) that determines the rate of conversion of the actual precursor of the one series prostaglandins (i.e. DGLA) into the precursor of the two series prostaglandins (i.e. arachidonic acid or AA) is under hormonal control (see Brenner, R. R.) In particular, insulin increases the activity of delta 5 desaturase (thereby increasing the production of AA and decreasing the levels of DGLA), whereas glucagon decreases its activity (thereby increasing DGLA levels and reducing the production of AA). The ratio of DGLA to AA determines extent of the production of prostaglandins of the one series or two series.

The enzyme activity delta 6 desaturase is the rate limiting step in Omega 6 essential fatty acid metabolism. This is why supplementation of the diet with activated Omega 6 essential fatty acids such GLA or DGLA can overcome any potential deficiency in this enzyme activity, thus ensuring that adequate levels of the precursors for the prostaglandins of the one series are available. However, it is the other key enzyme (delta 5 desaturase) in the metabolic cascade that is critical to determining which prostaglandin classes are ultimately formed. As disclosed in U.S. Pat. No. 5,059,622, eicosapentaenoic acid (EPA) or activated Omega 3 essential fatty acids that can be converted into EPA, can decrease the activity of the delta 5 desaturase enzyme. With appropriate combinations of EPA and GLA and/or DGLA, a modulation of prostaglandins can be achieved that are useful in treating hypertension. Although the presence of EPA can inhibit the delta 5 desaturase enzyme activity, the ratio of insulin to glucagon will have an even greater effect on the same enzyme activity. In particular, insulin will activate delta 5 desaturase whereas glucagon will inhibit its activity (see Brenner, R. R.). Therefore, a dietary composition that can maintain the optimal postprandial balance between glucagon and insulin levels at the time of oral supplementation with the correct ratio of activated Omega 6 and Omega 3 essential fatty acids will have a significant and beneficial effect on which prostaglandins (one series versus two series) are produced with the result being the reduction of hyperinsulinemia.

Figure 2:
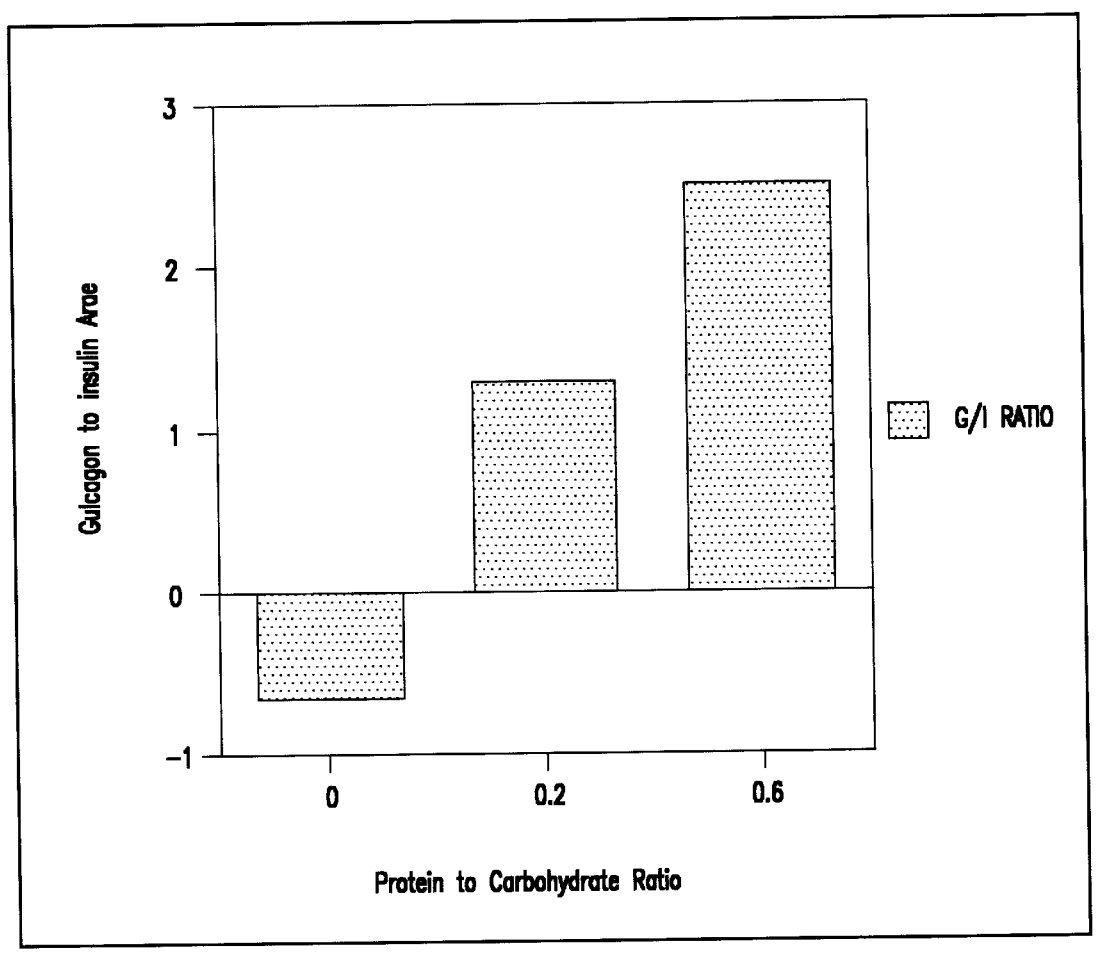
FIG. 2 shows the effect of protein to carbohydrate ratios on the postprandial ratio of secreted insulin and glucagon over a four hour period.

In FIG. 2, the data of Wesphal et al. has been replotted to show the impact of the protein to carbohydrate ratio on the relative rates of postprandial secretion of insulin and glucagon over an integrated four hour period. As seen from FIG. 2, the greater the protein to carbohydrate content of the meal, the greater is the resulting ratios of the four hour integrated areas of the glucagon secretion compared to insulin secretion. This creates a temporary favorable glucagon to insulin balance which enables the preferred modulation of prostaglandin production upon supplementation with the appropriate ratio of activated Omega 6 and Omega 3 essential fatty acids.

Figure 3:
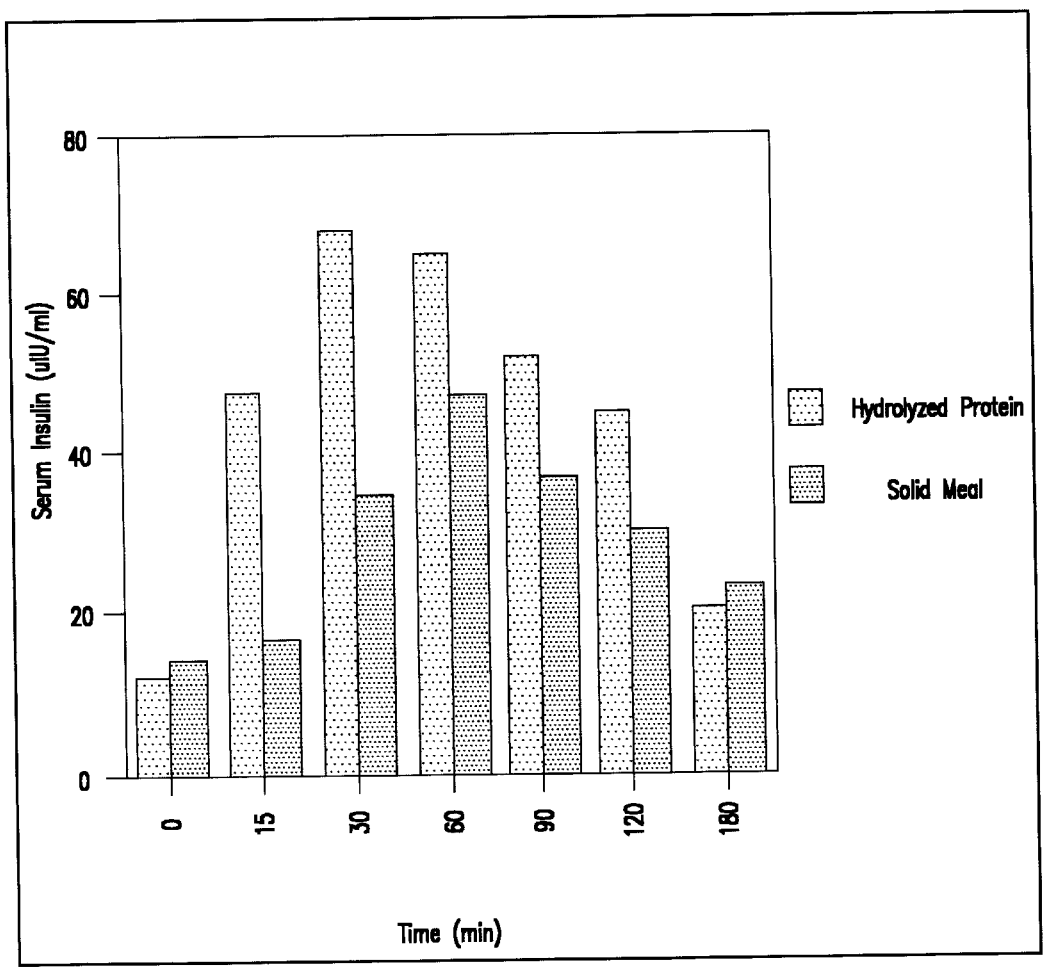
FIG. 3 shows the effect of hydrolyzed protein in a liquid meal versus non-hydrolyzed protein in a solid meal upon postprandial insulin secretion.

FIG. 3 shows the results of a study that compared the effect of protein in solid food format to partially hydrolzyed protein in a liquid meal format on the resulting postprandial insulin levels. This study shows that partially hydrolyzed protein in a liquid format will increase the levels of insulin to a much greater degree than use of the same amount of protein a solid food format. If hydrolyzed protein were used instead of non-hydrolyzed protein, then insulin levels would rise and glucagon levels will be decreased. As a consequence, the ratio of glucagon to insulin will be severely compromised using hydrolyzed protein as the protein component, and would result in an increased activity of the delta 5 desaturase enzyme and hence an increase in arachidonic acid production. U.S. Pat. No. 4,920,098 which teaches the use of hydrolyzed protein in a liquid format along with Omega 3 and Omega 6 essential fatty acids would provide a significantly reduced beneficial modulation of prostaglandins compared to this invention, and may even cause an overproduction of arachidonic acid which would lead to an increase of prostaglandins of the two series which would be contrary to purpose of this invention. As shown by Konrad et al., any increase in arachidonic acid formation will increase insulin secretion which would thus aggravate the existing hyperinsulinemia, not decrease it. Since U.S. Pat. No. 4,920,098 provided no clinical examples of their invention, this negative consequence of using hydrolyzed protein in the liquid format was not recognized.

Figure 4:
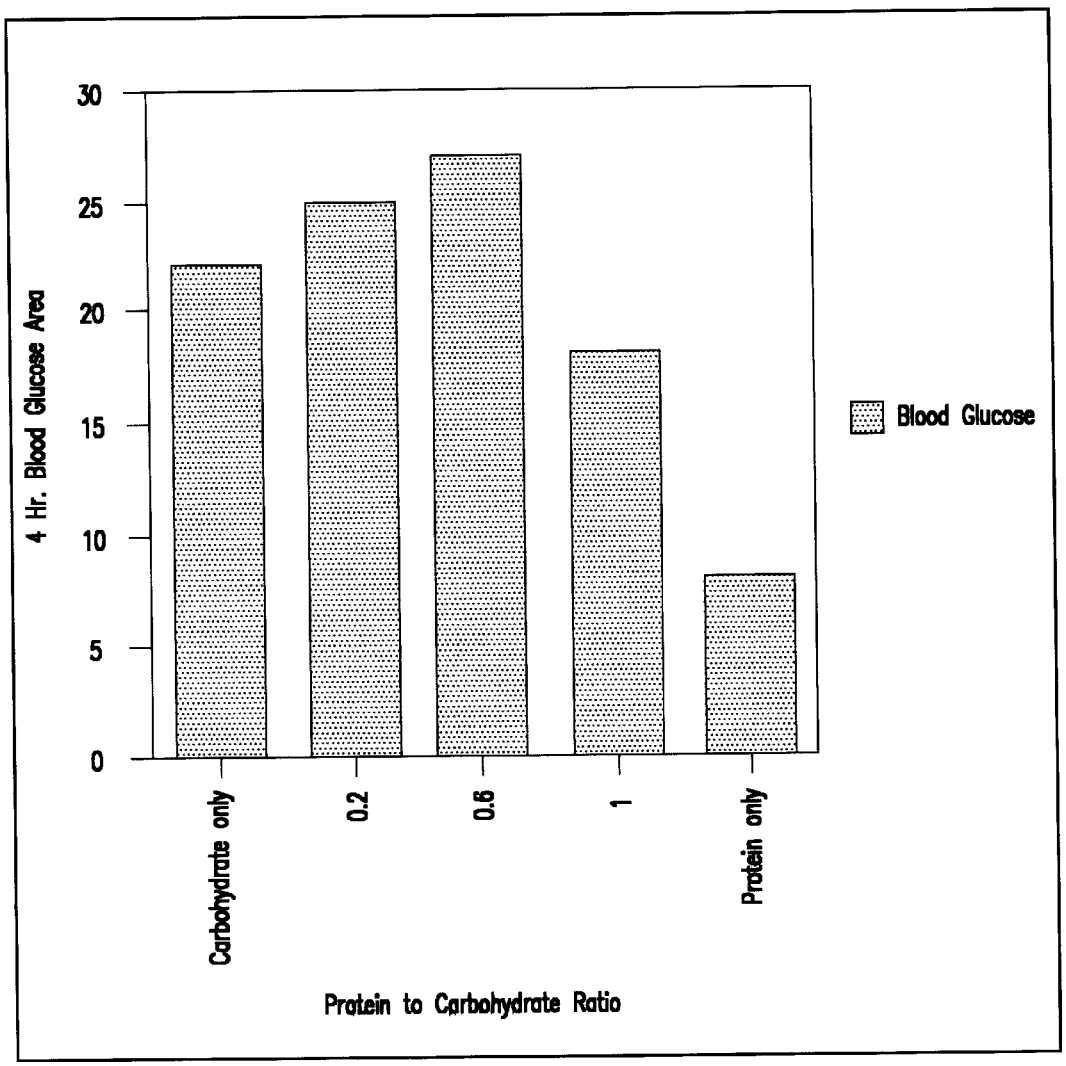
FIG. 4 shows the effect of protein to carbohydrate ratios on the postprandial blood sugar levels.

FIG. 4 shows the effect of having too high a protein to carbohydrate ratio in the solid food format. If the ratio of protein to carbohydrate in the solid food format is too high (greater than 1:1) then a state of ketosis would develop and glucagon secretion (important for the mobilization of stored liver glycogen to maintain blood sugar levels) would be diminished. This decrease in glucagon secretion due to ketosis would reduce the inhibition of the delta 5 desaturase activity, and therefore decrease the ability of the solid food format enhancement to the invention to correctly modulate prostaglandin production from the oral administration of the appropriate ratio of activated Omega 6 and Omega 3 essential fatty acids.

An example of this is shown in FIG. 4, which is also obtained from the data of Westphal et al. that shows that as the protein to carbohydrate ratio increases to 1:1 the resulting four hour integrated rise in blood sugar is reduced compared to lower protein to carbohydrate ratios. Since the maintenance of constant blood sugar levels is critical for homeostasis, the protein to carbohydrate ratio in the solid food format enhancement to the invention should be less than 1:1.

Figure 5:
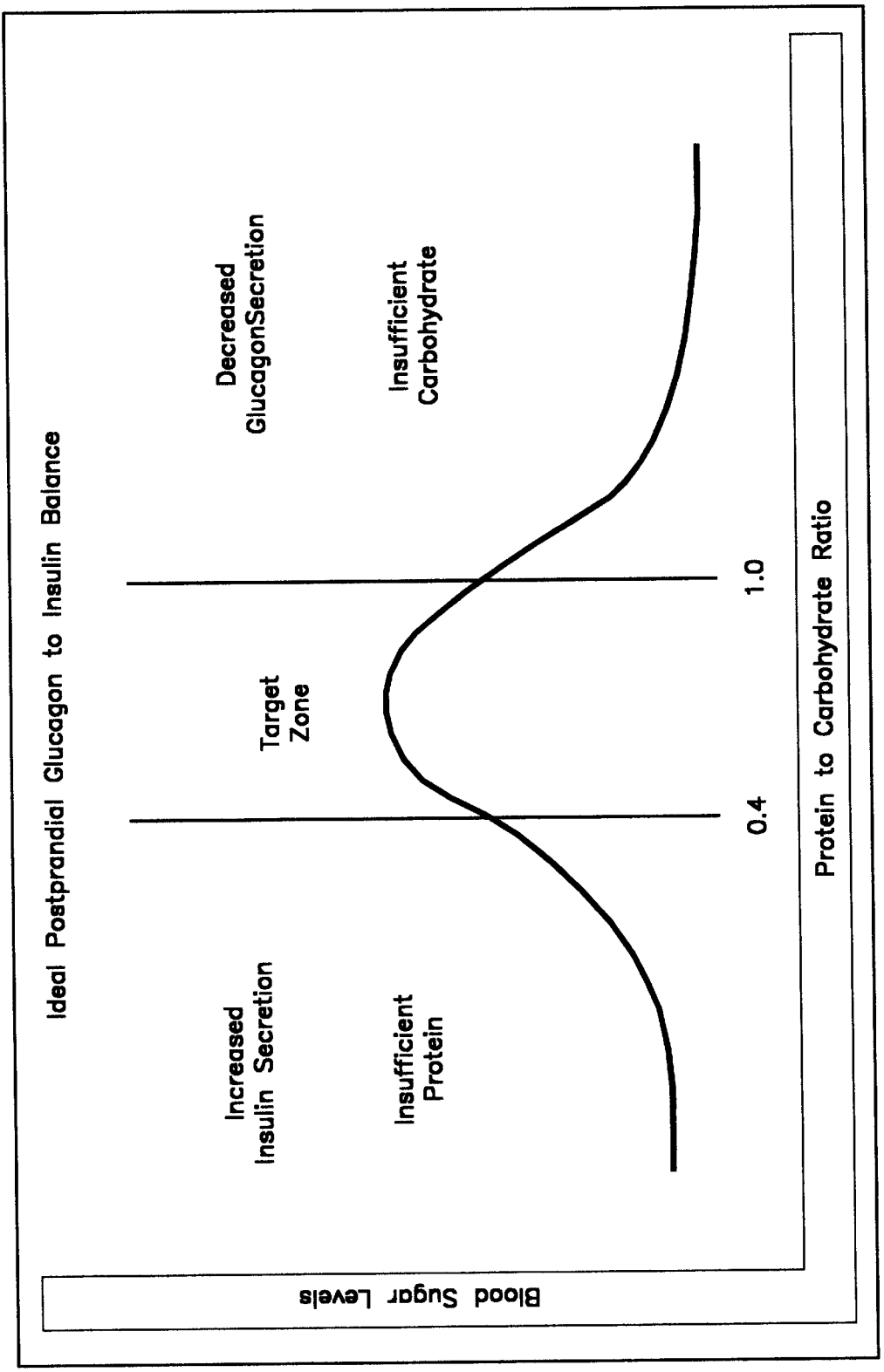
FIG. 5 is a schematic graphical representation of the the ideal protein to carbohydrate balance that will generate the optimal postprandial glucagon to insulin balance which in turn will modulate prostaglandin levels.

FIG. 5 is schematic representation of the ranges of protein to carbohydrate ratios that will maximize the postprandial glucagon to insulin ratio which will most effectively modulate the production of prostaglandins when the individual is supplied with the appropriate ratio of activated Omega 6 and Omega 3 essential fatty acids.

DETAILED DESCRIPTION OF THE EMBODIMENTS

The activated Omega 6 and Omega 3 essential fatty acids can be in the form of naturally occurring oils, triglycerides, free fatty acids, monoglycerides, diglycerides or alkyl esters. The activated essential fatty acids can be either included in the solid food format of the invention itself, or given separately in a suitable delivery form such as encapsulated in a soft gelatin capsule, emulsified oil, or as bulk oil. If the solid food enhancement to the invention is used, it must have the appropriate protein, carbohydrate, and fat composition in order to facilitate the proper postprandial balance of insulin and glucagon to maximize the production of the prostaglandins of the one series. The solid food format should be given within 1 hour of the dietary intake of the appropriate ratio of activated Omega 6 and Omega 3 essential fatty acids, if not at the same time.

The protein source in the solid food enhancement should consist of high quality protein which means having a complete range of essential amino acids. Preferable sources would include a mixture of soy protein and lactoalbumin, although other sources of high quality protein such as egg or microbiological sources can also be used. However whole protein, not hydrolyzates, of such high quality protein sources must be used in the invention since the use of hydrolyzed protein will increase the postprandial insulin levels (see FIG. 3) with a corresponding decrease in the postprandial glucagon levels.

The carbohydrate component of the solid food enhancement should consist of carbohydrates with a relatively low glycemic index so that increases in blood sugar and subsequent insulin secretion are kept to a minimum. Carbohydrates that contain fructose as a significant percentage of the total carbohydrate composition would be preferred sources. Such sources could be fructose, high fructose corn syrup, or other carbohydrates such as sucrose that contain fructose. Other carbohydrate sources that primarily contain glucose. maltose, or starch can be used in conjunction with the preferred fructose containing sources.

If the ratio of protein to carbohydrate in the solid food enhancement is too low (less than 0.4:1), then insulin levels will tend to rise which in turn will increase delta 5 desaturase activity and increase the production of AA which in turn increases insulin secretion (see Konrad et al.) and thereby would be contrary to the goal of this invention. If the protein to carbohydrate ratio in the solid food enhancement is too high (greater than 1:1) then ketosis can occur which would lower glucagon secretion.

The fat component of the solid food enhancement should consist of long chain triglycerides containing carbon atoms from 14 to 22 carbons in length. Medium chain triglycerides, such as those taught in U.S. Pat. No. 4,920,098 would not be a preferred source since their metabolism will induce the rapid formation of ketone bodies which would in turn reduce the secretion of glucagon [Bach, A.C. and Babayan, V. K. Amer. J. Clin. Nutr. 36 950–962 (1982)]. If the fat component of the solid food enhancement contains activated Omega 6 and Omega 3 essential fatty acids, then these Omega 3 essential fatty acids should either be in the form of stearidonic acid (which can be elongated into EPA), eicosapentaenoic acid (EPA), or docosahexaenoic acid (which can be retroconverted into EPA). If activated Omega 6 essential fatty acids (GLA or DGLA) are a constituent of the solid food format, then the amount of activated Omega 3 essential fatty acids should be at least equal to, if not greater than, the amount of activated Omega 6 essential fatty acids since the postprandial secretion of insulin and glucagon is being controlled by the solid food format. The reduced need for activated Omega 3 essential fatty acids such as EPA compared to U.S. Pat. No. 5,059,622 is due to the postprandial control of the insulin to glucagon balance using the appropriate protein to carbohydrate ratio in a solid format which will have a greater inhibition on delta 5 desaturase activity thereby reducing the need for increased levels of EPA to control the activity of the same enzyme.

Since the solid food enhancement of the invention can be used as a meal replacement, it is also desirable to include necessary vitamins and minerals. The levels of these vitamins and minerals should be greater than 25% of the RDA of vitamins and minerals in order to maintain relatively constant blood levels when the invention is being used as a meal replacement.

Although U.S. Pat. No. 4,920,098 discusses nutritional support for cardiovascular impaired individuals, this invention relates to a more defined nutritional compositions which are designed to modulate the production of prostaglandins of the one series. As an example, U.S. Pat. No. 4,920,098 teaches the use of hydrolyzed protein as a component of that invention. Furthermore, U.S. Pat. No. 4,920,098 teaches the use of a liquid formulation which would provide the maximum surface area for the digestive process. In either situation, the control of the postprandial balance of insulin and glucagon would not be achieved and subsequently the modulation of the physiological fate of the activated essential fatty acids could not be controlled.

To obtain optimal postprandial modulation of insulin and glucagon, the protein source of the solid food format should consist of between about 20% and 40% of total calories. Most preferably the protein source comprises approximately 30% of the total calories. The carbohydrate sources should contain approximately 30 to 50% of total calories. Most preferably, the carbohydrate source should contain approximately 40% of the total calories. The ratio of protein to carbohydrate should not be greater than 1:1 nor less than 0.4:1. The fat component should contain 20 to 40% of the total calories with the most preferable amount approximately being 30% of total calories. The most preferred balance of protein, carbohydrate, and fat (30%, 40%, and 30% of total calories respectively) in the solid food format enhancement of this invention is quite different than the preferred balance (20%, 50%, and 30% of total calories) taught in U.S. Pat. No. 4,920,098. The preferred ratio of protein to carbohydrate taught in U.S. Pat. No. 4,920,098 is too low to effect positively the postprandial insulin to glucagon ratio. Furthermore, as noted above, a liquid format for both enteral and parenteral formulations described in U.S. Pat. No. 4,920,098 will also prevent that nutritional composition from controlling insulin and glucagon levels because it is not in a solid format to slow digestion and subsequent macronutrient absorption. Also the use of hydrolyzed protein in the liquid format as taught in U.S. Pat. No. 4,920,098 would be contraindicated since it would cause an increase in insulin levels compared to this invention. These increased insulin levels would decrease the desired modulation of prostaglandins and would not reduce hyperinsulinemia, and in fact may even increase it.

If activated Omega 6 essential fatty acids are included in the fat component of the solid food format, then the ratio of activated Omega 3 essential fatty to the total activated Omega 6 essential fatty acids should be at least greater than 1:1. If the solid food format consisting of protein and carbohydrate is not used with the activated essential fatty acids, then the ratio of activated Omega 3 essential fatty acids to activated Omega 6 essential fatty acids should be greater that 2:1 as taught in U.S. Pat. No. 5,059,622.

The cardiovascular disease conditions that can be treated by the invention by way of example and illustration, and not limitation, include the following: diabetes (Type I and Type II), hypertension, hyperlipidemia, obesity, congestive heart failure, angina, increased platelet aggregation, and obesity.

Examples will now be given. However, it is recognized that various changes and modifications to the illustrated examples can be made by those persons skilled in the art, all falling within the spirit and scope of the invention.

EXAMPLE 1

A soft gelatin capsule containing 40 mg. of refined borage oil, 333 mg. of refined marine oil, and 120 mg. of olive oil would contains 80 mg. of EPA and 10 mg. of GLA. This soft gelatin capsule can be given orally for the reduction of hyperinsulinemia.

EXAMPLE 2

A soft gelatin capsule containing 10 mg. of the ethyl ester of DGLA and 333 mg. of refined marine oil would contain 10 mg. of DGLA and 80 mg. of EPA. This soft gelatin capsules can be given orally for the reduction of hyperinsulinemia.

EXAMPLE 3

A solid food format in a bar form containing 14 grams of protein consisting of soy protein, calcium casineate, peanuts (31% of calories), 18 grams of carbohydrate consisting of high fructose corn syrup, honey, sucrose, and fructose (40% of calories), and fat consisting of olive oil, borage oil (a source of GLA), marine oil (a source of EPA) and palm kernel oil (29% of calories). The amount of GLA (5 mg.) and of EPA (5 mg.) in the bar gives a 1:1 ratio. The bar also contains the following vitamin and mineral contents with the per cent U.S. Recommended Daily Allowance (RDA) in parenthesis: A(50), B1(48), B2 (46), B3 (100), B6 (200), B12 (33), C (200), D (34),E (200), Folic acid (33), D-pantothenic acid (33), Biotin (30), Calcium (32), Phosphorus (28), Iron (33), Zinc (50), Magnesium (35), Iodine (40), Copper (43), Chromium (100 ug*), Manganese (1.3 mg.*). The asterisk means that no U.S. RDA has been established.

EXAMPLE 4

A solid food format in a bar form containing 14 grams. of protein consisting of toasted soy beans, soybean isolate, whey protein concentrate, and calcium caseinate. (31% of calories), 18 grams of carbohydrate consisting of raisin paste, honey, high fructose corn syrup, and high maltose corn syrup (40% of calories), and fat consisting of sesame oil, marine oil (source of EPA), black currant oil (source of GLA), and palm kernel oil (29% of calories). The amount EPA (80 mg.) and GLA (5 mg.) in the bar gives a 16:1 ratio. The bar also contains the following vitamin and mineral contents with the per cent U.S. Recommended Daily Allowance (RDA) in parenthesis: A(50), B1(48), B2 (46), B3

(100), B6 (200), B12 (33), C (200), D (34),E (200), Folic acid (33), D-pantothenic acid (33), Biotin (30), Calcium (32), Phosphorus (28), Iron (33), Zinc (50), Magnesium (35), Iodine (40), Copper (43), Chromium (100 ug*), Manganese (1.3 mg.*). The asterisk means that no U.S. RDA has been established.

EXAMPLE 5

A solid food format in a bar form containing 14 g. of protein consisting of soy protein, calcium casineate, peanuts (31% of calories), 18 grams of carbohydrate consisting of high fructose corn syrup, honey, sucrose, and fructose (40% of calories), and fat consisting of olive oil and palm kernel oil (29% of calories). This bar contains no activated Omega 3 or Omega 6 essential fatty acids. The bar also contains the following vitamin and mineral contents with the per cent U.S. Recommended Daily Allowance (RDA) in parenthesis: A(50), B1(48), B2 (46), B3 (100), B6 (200), B12 (33), C (200), D (34),E (200), Folic acid (33), D-pantothenic acid (33), Biotin (30), Calcium (32), Phosphorus (28), Iron (33), Zinc (50), Magnesium (35), Iodine (40), Copper (43), Chromium (100 ug*), Manganese (1.3 mg.*). The asterisk means that no U.S. RDA has been established.

EXAMPLE 6

Elevated triglyceride levels are strongly associated with hyperinsulinemia (see Reaven, G. M.). This is because the a key enzyme (acetyl-CoA carboxylase) that is the first step of fatty acid biosynthesis in the liver is activated by insulin (Mabrouk, G. M., et al. *J. Biol. Chem.* 265 6330–6338 (1990). A patient with triglycerides levels of 467 mg./dl was put on a dietary regime of two solid food bars per day as a meal replacement using a composition found in Example 5. With each bar two soft gelatin capsules containing activated essential fatty acids were taken. The capsules, each containing 60 mg. EPA and 15 mg. of GLA, were consumed with each bar.

After six weeks, the triglyceride level of the patient had decreased to 167 mg./dl. The patient was taken off the bars and capsules containing the activated essential fatty acids, and her triglyceride levels after 6 weeks rose to 432 mg./dl. The reduction of elevated triglycerides levels is consistent with a lowering of hyperinsulinemia.

EXAMPLE 7

Hypertension is strongly associated with hyperinsulinemia (see Reaven, G. M.). A patient had a blood pressure of 180/110. Using the composition described in Example 3 given twice per day as a meal replacement along with two soft gelatin capsules, each capsule containing 80 mg. EPA and 10 mg. GLA, with each bar. The total intake of EPA and GLA per day was 170 mg. and 30 mg. GLA respectively. The blood pressure was reduced to 110/70 within six weeks. The reduction of hypertension is consistent with a reduction the associated hyperinsulinemia.

EXAMPLE 8

Type II diabetes is strongly associated with hyperinsulinemia (see Reaven, G. M.). Using the composition in Table 3, a bar along a single soft gelatin capsules containing a total of 80 mg. EPA and 5 mg. GLA were consumed twice per day as a meal replacement. The patient with Type II diabetes was able to reduce her fasting blood sugar from 150 mg./dl. to 107 mg./dl. after 5 weeks. The reduction of fasting blood sugar is consistent with a reduction of the associated hyperinsulinemia.

EXAMPLE 9

Hyperinsulinemia results in insulin resistance (see Reaven, G. M.). The two primary serum indicators of insulin resistance is fasting serum glucose and fasting serum triglycerides. A two week study was conducted with the composition of Example 4 using six males. The composition was taken twice per day. At the end of two weeks, the average serum glucose had decreased from 99.5±5.3 to 82.5±4.9. This represents a 17% decrease in fasting glucose levels which had a statistical significance of $p<0.005$. Serum triglycerides decreased from 189.3±54.7 to 138.2±37.9 in the same time period. This represents a 30% decrease in fasting triglyceride levels with a statistical significance of $p<0.05$. The reductions in fasting glucose and fasting triglycerides levels are consistent with a reduction in elevated insulin levels.

EXAMPLE 10

The development of hyperinsulinemia often leads to increases in platelet aggregation [Winocour, P. D. *Diabetes* 41 26–31 (1992)]. To determine the effect on platelet aggregation of individuals without existing cardiovascular disease, ten normal individuals consumed eight soft gelatin capsules containing 80 mg. EPA and 10 mg. GLA per day (640 mg. EPA and 80 mg. GLA per day) for a two week period. Platelet aggregation times of each subject were determined prior to and after dietary intervention with the invention. The platelet aggregation was initiated with exposure to collagen or with the thromboxane $A_2$ agonist U46619. Platelet aggregation initiated by U46619 was decreased by 24% ($p<0.01$) compared to the starting values, and the lag time for the onset of platelet aggregation by exposure to collagen was increased by 20% ($p>0.05$). The reduction of platelet aggregation is consistent with a reduction in the circulating levels of insulin.

EXAMPLE 11

Excess body fat is highly correlated with hyperinsulinemia. Ten males with an average per cent body fat of 33.4±1.2% used the composition listed in Example 5 plus two soft gelatin capsules, each containing 80 mg. EPA and 10 mg. of GLA, twice a day as a meal replacement. After a total of 8 weeks, their average per cent body fat had decreased to 26.4±1.4%. This represents a 21% decrease in body fat with a statistical significance of $p<0.005$. The decrease in per cent body fat is consistent with a reduction of hyperinsulinemia.

EXAMPLE 12

Twenty women with an average per cent body fat of 36.8±3.2% using the composition in Example 2 twice per day as a meal replacement. After 8 weeks, their average per cent body fat had decreased to 29.5±4.1. This represented a 19% decrease in their body fat with a statistical significance of $p<0.005$. The reduction in the body fat is consistent with a reduction in hyperinsulinemia.

EXAMPLE 13

Insulin resistance due to hyperinsulinemia is commonly associated with increased glycosation of hemoglobin ($Hb_{A1C}$) due to increased serum glucose levels. Hyperinsulinemia is also associated with increased triglycerides, decreased HDL cholesterol levels, and elevated percent body fat (see Reaven, G. M.). A male subject with a body fat percentage of 34.8%, a triglyceride level of 450 mg./dl, a $Hb_{A1C}$ level of 6.8% of total hemoglobin, and HDL cholesterol level of 24 mg./dl used two capsules, each capsule contained 80 mg. EPA and 10 mg. GLA, twice a day. The capsules were taken with the composition described in Example 5 as a meal replacement to enhance the action of the activated essential fatty acids. After five weeks of treatment, his body fat had decreased to 30%, his triglycerides levels had decreased to 168 mg./dl., his $Hb_{A1C}$ level decreased to 5.3% of total hemoglobin, and HDL cholesterol increased to 30 mg./dl. These changes in body fat and these blood parameters is consistent with a reduction in hyperinsulinemia.

EXAMPLE 14

Fatigue is a common result from cardiovascular deterioration especially in congestive heart failure. It is also common as a consequence of postviral infection such as viral myocarditis. To demonstrate the ability of the invention to treat fatigue, we used HIV infected patients who had developed chronic fatigue. The patients self rated their fatigue using a five level score to determine changes in fatigue levels with treatment. These levels ranged from +2 (significant reduction of fatigue) to -2 (significant increase in fatigue), with a level of 0 indicating no change in fatigue status.

Patients in each group received soft gelatin capsules containing 80 mg. EPA and 10 mg. GLA (active) or placebo capsules containing olive oil. Each group took 10 capsules per day. After six months those taking the active capsules had a fatigue rating of (+1.1), whereas those on the placebo capsules had a fatigue rating of (-0.5). The differences between the two groups was statistically significant. When the patients taking the placebo capsules were switched to the active capsules, their fatigue rating changed from -0.5 to +0.8. This result was also statistically significant. This example indicates that cardiovascular fatigue can be alleviated by the invention.

EXAMPLE 15

Another example of the benefits of the invention, would be for patients who are taking medication, which as a side effect, will increase their fatigue. An example of such medication is AZT which causes anemia when taken by HIV positive individuals at a dosage of 1500 mg. AZT per day. The active group took 10 soft gelatin capsules per day. Each capsule of the active contained 60 mg. EPA and 15 mg. of GLA. The control group took 10 capsules per day consisting of olive oil as a placebo. Fatigue ratings were as discussed in Example 14. After six months, those on the active had a fatigue rating of +1.0 whereas those on the placebo had a fatigue rating of -0.4. The differences between the two groups was statistically significant. Those in the placebo group were then placed on the active capsules for 5 months. At the end of five months, their fatigue rating had changed from -0.4 to +0.5. These results indicate that the invention can alleviate drug induced fatigue.

EXAMPLE 16

An example of a pharmaceutical composition is the addition of an existing drug to the invention. Aspirin is a known anti-platelet aggregation drug. Since the invention has been shown to reduce platelet aggregation (see Example 10, the addition of aspirin would be synergistic. An appropriate pharmaceutical composition is the addition of 50 mg. of aspirin to a soft gelatin capsule containing 80 mg. of EPA and 10 mg. of GLA. These capsules can be combined with or without the solid food format to reduce platelet aggregation.

EXAMPLE 17

Beta blockers are often used to treat hypertension. An appropriate example of a pharmaceutical composition would be the following: 5 mg. of propranodol is formulated in a soft gelatin capsule containing 60 mg. EPA and 15 mg. of GLA. This formulation would then be used with or without the bar composition described in Example 5 to treat a patient with hypertension.

EXAMPLE 18

Fatigue is a result of congestive heart failure. Angiotensin I converting enzyme inhibitors such as captopril are used to treat such heart failure. An appropriate example of pharmaceutical composition would be the following: 5 mg. of captopril included in a solid food format similar to that described in Example 4 but which containing 30 mg. EPA and 5 mg. of GLA for use with patients with congestive heart failure.

What is claimed is:

1. A method for the reduction of hyperinsulinemia in a person by the control of insulin and glucagon levels, which method comprises:

a) providing for the oral introduction into the person of a therapeutic, effective amount of a solid food product having a total calorie value, which solid food product comprises:
      i) a protein source of high biological value having about 20 to 40% of total calorie value;
      ii) a carbohydrate source composed primarily of a low glycemic index having about 30 to 50% of total calorie value;
      iii) a fat source having about 20 to 40% of total calorie value wherein the fat source comprises a combination of activated Omega 6 essential fatty acids and activated Omega 3 essential fatty acids in a ratio of Omega 3 acids to Omega 6 acids of greater than 2:1; and
      iv) the protein source to carbohydrate source ratio greater than 0.4:1, but less than 1:1, to control the insulin and glucagon levels of the person.

2. The method of claim 1 which includes incorporating all or a portion of the fat source in a separate form for the introduction with the solid food product.

3. The method of claim 1 wherein the fat source comprises a ratio of Omega 3 acids to Omega 6 acids from 2:1 to 8:1.

4. The method of claim 1 wherein the Omega 6 fatty acids are selected from the group consisting of gamma linolenic acid, dihomo gamma linolenic acid and their alkyl esters.

5. The method of claim 1 wherein the Omega 3 fatty acids are selected from the group consisting of eicosapentaenoic acid and its alkyl esters.

6. The method of claim 1 which includes reducing the blood pressure of a hypertensive person.

7. The method of claim 1 which includes providing for the oral ingestation by the person of the fat source in an emulsion, microencapsulated or capsule form.

8. The method of claim 1 wherein the carbohydrate source comprises fructose or a fructose source.

9. The method of claim 1 wherein the activated Omega 6 essential fatty acid comprises gamma linolenic acid (GLA) or dihomo gamma linolenic acid (DGLA) in the form of triglycerides, diglycerides, monoglycerides, free fatty acids or their alkyl esters.

10. The method of claim 1 wherein the activated Omega 3 essential fatty acid comprises eicosapentaenoic acid (EPA), stearidonic acid, or docosahexenoic acid in the form of triglycerides, diglycerides, monoglycerides, free fatty acids, or their alkyl esters.

11. A solid food nutritional composition adapted for oral administration to a person to reduce hyperinsulinemia, which composition comprises:
   a) a protein source of high biological value having about 20 to 40% of total calorie value;
   b) a carbohydrate source composed primarily of a low glycemic index having about 30 to 50% of total calorie value;
   c) a fat source having about 20 to 40% of total calorie value wherein the fat source comprises a combination of activated Omega 3 essential fatty acids and activated Omega 6 essential fatty acids in a ratio of Omega 3 acids to Omega 6 acids of greater than 2:1; and
   d) the protein source to carbohydrate source greater than 0.4:1, but less than 1:1, to control the insulin and glucagon levels of the person.

12. The composition of claim 11 wherein the fat source comprises a ratio of Omega 3 acids to Omega 6 acids from 2:1 to 8:1.

13. The composition of claim 11 wherein the Omega 6 fatty acids are selected from the group consisting of gamma linolenic acid, dihomo gamma linolenic acid and their alkyl esters.

14. The composition of claim 11 wherein the carbohydrate source comprises fructose or a fructose source.

15. The composition of claim 11 wherein the activated Omega 6 essential fatty acid comprises gamma linolenic acid (GLA) or dihomo gamma linolenic acid (DGLA) in the form of triglycerides, diglycerides, monoglycerides, free fatty acids or their alkyl esters.

16. The composition of claim 11 wherein the activated Omega 3 essential fatty acid comprises eicosapentaenoic acid (EPA), stearidonic acid, or docosahexenoic acid in the form of triglycerides, diglycerides, monoglycerides, free fatty acids, or their alkyl esters.

* * * * *